(12) United States Patent
Mirov et al.

(10) Patent No.: US 10,518,039 B2
(45) Date of Patent: Dec. 31, 2019

(54) APPARATUS AND METHODS FOR TRACKING ADMINISTERING OF MEDICATION BY MEDICATION INJECTION DEVICES

(71) Applicant: Verily Life Sciences LLC, Mountain View, CA (US)

(72) Inventors: Russell Mirov, Los Altos, CA (US); Benjamin David Krasnow, Redwood City, CA (US); Peter Howard Smith, Pacifica, CA (US); Travis Deyle, San Jose, CA (US); Brett Schleicher, San Francisco, CA (US)

(73) Assignee: Verily Life Sciences LLC, South San Francisco, CA (US)

(*) Notice: Subject to any disclaimer, the term of this patent is extended or adjusted under 35 U.S.C. 154(b) by 141 days.

(21) Appl. No.: 15/333,770

(22) Filed: Oct. 25, 2016

(65) Prior Publication Data

US 2017/0312445 A1 Nov. 2, 2017

Related U.S. Application Data

(60) Provisional application No. 62/329,605, filed on Apr. 29, 2016.

(51) Int. Cl.
*A61M 5/315* (2006.01)
*G06F 19/00* (2018.01)
*A61M 5/142* (2006.01)

(52) U.S. Cl.
CPC ........ *A61M 5/31568* (2013.01); *A61M 5/142* (2013.01); *A61M 5/315* (2013.01);
(Continued)

(58) Field of Classification Search
CPC .............. A61M 5/315; A61M 5/31511; A61M 5/31568; A61M 5/31573; A61M 2205/3375
See application file for complete search history.

(56) References Cited

U.S. PATENT DOCUMENTS

| 4,817,044 A | 3/1989 | Ogren |
| 5,303,585 A * | 4/1994 | Lichte ................. G01F 25/0061 367/908 |

(Continued)

FOREIGN PATENT DOCUMENTS

| CA | 2 604 498 A1 | 10/2006 |
| EP | 2 777 731 A1 | 9/2014 |

(Continued)

OTHER PUBLICATIONS

International Application No. PCT/US2017/023653—International Search Report and Written Opinion dated Jun. 2, 2017, 14 pages.

(Continued)

*Primary Examiner* — Amber R Stiles
*Assistant Examiner* — James D Ponton
(74) *Attorney, Agent, or Firm* — Christensen O'Connor Johnson Kindness PLLC

(57) ABSTRACT

Various apparatuses and methods for tracking the administration of medication by medication injection devices are provided. A plunger head for a medication injection device may include a first component that houses electronic components and a second component that couples to the first component to form the plunger head. When the plunger head is installed within a barrel of the medication injection device the second component may separate the first component from medication contained within the barrel.

20 Claims, 10 Drawing Sheets

(52) U.S. Cl.
CPC ...... *G06F 19/3418* (2013.01); *G06F 19/3468* (2013.01); *A61M 2205/3368* (2013.01); *A61M 2205/3375* (2013.01); *A61M 2205/3553* (2013.01); *A61M 2205/3584* (2013.01); *A61M 2205/3592* (2013.01); *A61M 2205/50* (2013.01); *A61M 2205/52* (2013.01); *A61M 2207/00* (2013.01); *A61M 2230/201* (2013.01)

(56) References Cited

U.S. PATENT DOCUMENTS

| | | | |
|---|---|---|---|
| 5,720,733 | A | 2/1998 | Brown |
| 5,757,244 | A | 5/1998 | Nonaka et al. |
| 6,368,314 | B1 | 4/2002 | Kipfer et al. |
| 7,922,458 | B2 | 4/2011 | Rush et al. |
| 7,993,108 | B2 | 8/2011 | Rush et al. |
| 7,993,109 | B2 | 8/2011 | Rush et al. |
| 8,029,245 | B2 | 10/2011 | Rush et al. |
| 8,029,250 | B2 | 10/2011 | Rush et al. |
| 8,047,812 | B2 | 11/2011 | Rush et al. |
| 8,075,490 | B2 | 12/2011 | Lofgren et al. |
| 8,708,957 | B2 | 4/2014 | Jespersen et al. |
| 9,186,465 | B2 | 11/2015 | Jorgensen et al. |
| 9,289,551 | B2 | 3/2016 | Hata et al. |
| 9,308,324 | B2 | 4/2016 | Shaanan et al. |
| 9,314,573 | B2 * | 4/2016 | Nielsen .................. A61M 5/24 |
| 9,672,328 | B2 | 6/2017 | Saint et al. |
| 9,907,902 | B2 * | 3/2018 | Mitrosky .......... A61M 5/31525 |
| 2001/0034506 | A1 | 10/2001 | Hirschman et al. |
| 2005/0238503 | A1 | 10/2005 | Rush et al. |
| 2005/0258182 | A1 | 11/2005 | Anderson |
| 2007/0060820 | A1 * | 3/2007 | Lofgren ............... A61B 5/0215 600/481 |
| 2009/0105648 | A1 | 4/2009 | Rush et al. |
| 2009/0105649 | A1 | 4/2009 | Rush et al. |
| 2009/0112156 | A1 | 4/2009 | Rush et al. |
| 2009/0112165 | A1 | 4/2009 | Rush et al. |
| 2009/0163869 | A1 | 6/2009 | Rush et al. |
| 2011/0270214 | A1 | 11/2011 | Jorgensen et al. |
| 2012/0083730 | A1 | 4/2012 | Rush et al. |
| 2012/0165755 | A1 * | 6/2012 | Chattaraj ........... A61M 5/31511 604/222 |
| 2012/0195182 | A1 * | 8/2012 | Pommereau ....... A61M 5/31511 369/127 |
| 2013/0072897 | A1 | 3/2013 | Day et al. |
| 2014/0288408 | A1 | 9/2014 | Deutsch |
| 2015/0051538 | A1 | 2/2015 | Hata et al. |
| 2015/0165114 | A1 | 6/2015 | Grant et al. |
| 2015/0174342 | A1 | 6/2015 | Mitrosky et al. |
| 2015/0202375 | A1 | 7/2015 | Schabbach et al. |
| 2015/0217059 | A1 * | 8/2015 | Ashby ............... A61M 5/31511 604/189 |
| 2015/0273129 | A1 | 10/2015 | Freeman et al. |
| 2015/0289895 | A1 | 10/2015 | Gomi et al. |
| 2015/0289896 | A1 | 10/2015 | Gomi et al. |
| 2016/0012205 | A1 | 1/2016 | Saint et al. |
| 2016/0022539 | A1 | 1/2016 | Daines |
| 2016/0213856 | A1 | 7/2016 | Despa et al. |
| 2016/0259913 | A1 | 9/2016 | Yu et al. |
| 2017/0049969 | A1 * | 2/2017 | Dunne ................ A61M 5/2033 |
| 2017/0189625 | A1 | 7/2017 | Cirillo et al. |
| 2017/0216528 | A1 | 8/2017 | Pommereau et al. |
| 2017/0270276 | A1 | 9/2017 | Saint et al. |
| 2017/0316157 | A1 | 11/2017 | Riedel et al. |
| 2018/0001009 | A1 | 1/2018 | Crawford et al. |
| 2019/0022306 | A1 | 1/2019 | Gibson et al. |

FOREIGN PATENT DOCUMENTS

| | | |
|---|---|---|
| WO | 2007/000680 A2 | 1/2007 |
| WO | 2007/024193 A2 | 3/2007 |
| WO | 2010/052275 A2 | 5/2010 |
| WO | 2010/133676 A1 | 11/2010 |
| WO | 2011/089205 A2 | 7/2011 |
| WO | 2013/054165 A1 | 4/2013 |
| WO | 2014/028936 A1 | 2/2014 |
| WO | 2014/145906 A2 | 9/2014 |
| WO | 2016/007935 A2 | 1/2016 |
| WO | WO 2016/062605 A1 | 4/2016 |
| WO | 2016/122974 A1 | 8/2016 |

OTHER PUBLICATIONS

International Search Report and Written Opinion from the International Searching Authority dated Mar. 5, 2018, for International Application No. PCT/US2017/063768, filed Nov. 29, 2017, 16 pages.

International Preliminary Report on Patentability and Written Opinion dated Oct. 30, 2018 for International Application No. PCT/US2017/025085, filed Mar. 30, 2017, 9 pages.

International Preliminary Report on Patentability and Written Opinion dated Oct. 30, 2018 for International Application No. PCT/US2017/030068, filed Apr. 28, 2017, 14 pages.

English Translation of Chinese Office Action for corresponding Chinese Patent Application No. 201790000809.1, dated Jul. 11, 2019, pp. 1-3.

International Preliminary Report on Patentability and Written Opinion dated Oct. 30, 2018 for International Application No. PCT/US2017/023653, filed Mar. 22, 2017, 8 pages.

International Search Report and Written Opinion dated Aug. 11, 2017, in International Application No. PCT/US2017/030068, filed Apr. 28, 2017, 20 pages.

International Search Report and Written Opinion dated Jul. 17, 2017, in International Application No. PCT/US2017/025085, 15 pages.

Office Action dated Jun. 18, 2019, issued in corresponding Chinese Application No. 201790000802.X, filed Oct. 29, 2018, 5 pages.

* cited by examiner

US 10,518,039 B2

APPARATUS AND METHODS FOR TRACKING ADMINISTERING OF MEDICATION BY MEDICATION INJECTION DEVICES

RELATED APPLICATIONS

This application claims the benefit of U.S. Provisional Application No. 62/329,605, filed Apr. 29, 2016, which is incorporated by reference in its entirety.

TECHNICAL FIELD

The present disclosure relates generally to the field of tracking the administration of medication, and more particularly, apparatus and methods for tracking the administration of medication by medication injection devices.

BACKGROUND DESCRIPTION

Measuring the quantity and recording the timing of a drug's administration is an integral part of many disease treatments. For many treatments, to achieve the best therapeutic effect, specific quantities of a drug may need to be injected specific times of day. For example, individuals suffering from diabetes may be required to inject themselves regularly throughout the day in response to measurements of their blood glucose. The frequency and volume of insulin injections must be carefully tracked and controlled to keep the patient's blood glucose level within a healthy range. Currently, there are a limited number of methods or devices for automatically tracking the drug administration without requiring the user to manually measure and record the volume, date, and time. A variety of glucose injection syringes/pens have been developed, but there is much room for significant advancement in the technology in order to reduce the size, lower the cost, and enhance the functionality and reliability thus making them a more viable long-term solution. For example, current insulin pens are often disposable, but do not include dosage tracking. A smaller portion of the market is composed of reusable pens which are more expensive, and still don't include good dosage tracking capabilities.

SUMMARY

The present disclosure is directed to apparatuses and methods of drug administration using a medication injection device.

In one aspect, the present disclosure is directed to a plunger head for a medication injection device. The plunger head may include a first component having electronic components housed within and a second component at least partially surrounding the first component. The second component may separate the first component from medication contained within a barrel of the medication injection device.

In another aspect, the present disclosure is directed to a method of manufacturing a plunger head for a medication injection device. The method may include assembling a first component of the plunger head, which houses electronic components, using lower-temperature assembly steps. The method may also include sterilizing the first component using a lower-temperature sterilization method. The method may further include molding a second component of the plunger head from an elastomer to define a bucket shape. The method may also include sterilizing the first component using a higher-temperature sterilization method. The method may further include attaching the first component to the second component to form the plunger head.

In another aspect, the present disclosure is directed to a method of assembling a plunger head for a medication injection device, wherein the plunger head includes a plurality of electronic components. The method may include combining a first component and a second component of the plunger head, wherein at least a portion of the electronic components are housed in the first component.

DETAILED DESCRIPTION

Reference will now be made in detail to embodiments of the present disclosure, examples of which are illustrated in the accompanying drawings. Where possible, the same reference numbers will be used throughout the drawings to refer to the same or like parts.

Figure 1:
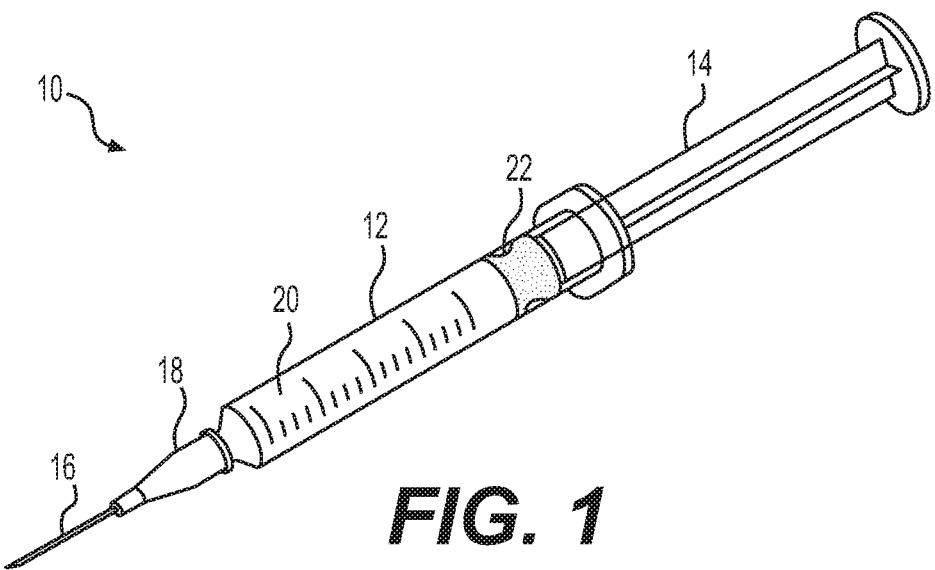
FIG. 1 is a perspective view of a medication injection device, which includes a plunger head according to an exemplary embodiment.

FIG. 1 shows a perspective view of a medication injection device in the form of a syringe 10 designed for ejecting a fluid. Syringe 10 may include a barrel 12, a plunger 14, a needle 16, and a hub 18 connecting needle 16 to barrel 12. Barrel 12 may be configured to contain a fluid, for example, a medication 20 and syringe 10 may be configured to dispense medication 20 from needle 16 when plunger 14 is depressed. A standard syringe usually contains a plunger head at the end of the plunger that seals the top of the barrel and forces the fluid out the needle when the plunger is depressed. The plunger head for a standard syringe is usually just a piece of molded rubber.

For syringe 10 shown in FIG. 1, the standard plunger head has been replaced with a smart or intelligent plunger head 22 that is configured to measure and register the quantity of medication 20 administered and the time and date of administration. Plunger head 22 may be installed in a standard syringe by withdrawing plunger 14 and replacing the standard plunger head with smart plunger head 22. In some embodiments, syringe 10 may be manufactured and supplied with a smart plunger head 22 preinstalled. Smart plunger head 22 may be referred herein as either smart plunger head 22 or plunger head 22. It is contemplated that for other types of medication injection devices, which may include or use plunger head 22, plunger head 22 may replace a standard plunger head supplied with the device or plunger head 22 may be supplied with the device.

Plunger head 22 may be sized to correspond with the size of barrel 12. For example, plunger head 22 may be formed to fit any size syringe. For example, plunger head 22 may be sized to fit a 1 ml, 2 ml, 3 ml, 5 ml, 10 ml, 20 ml, 30 ml, or 50 ml syringe. Plunger head 22 may also be adapted to fit a variety of other medication injection devices.

Figure 2:
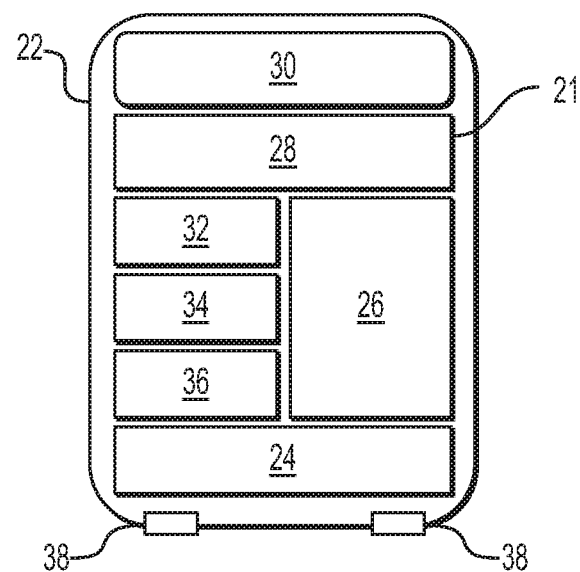
FIG. 2 is a schematic of the plunger head of FIG. 1.

FIG. 2 shows a schematic of plunger head 22, according to an exemplary embodiment. Plunger head 22 may include a transducer 24, a microcontroller 26, a power source 28, and an antenna (e.g., for near field communication (NFC) or a transceiver 30 (e.g., for BLUETOOTH low energy (BLE) communication). In some embodiments, plunger head 22 may also include a temperature sensor 36. Temperature sensor 36 may be configured to measure the ambient temperature, which may be generally representative of a temperature of plunger head 22 and/or medication 20.

Transducer 24 may be configured to send and receive ultrasonic signals. Microcontroller 26 may be programmed with instructions to control the overall operation of plunger head 22. Transceiver 30 may be configured to wirelessly communicate with a remote device (e.g., a smart phone, a glucose monitor, an insulin pump, or a computer) using one or more wireless communication methods. The one or more wireless communication methods may include, for example, radio data transmission, Bluetooth, BLE, near field communication (NFC), infrared data transmission, electromagnetic induction transmission, and/or other suitable electromagnetic, acoustic, or optical transmission methods. Power source 28 may be configured to power transducer 24, microcontroller 26, transceiver 30, temperature sensor 36, and other electronic components of plunger head 22.

In some embodiments, as shown in FIG. 2, the components of plunger head 22 may be at least partially encapsulated in a polymer 21 (e.g., elastomer, rubber, ethylene propylene (EPM), Nitrile (NBR), ethylene propylene diene (EPDM), polybutadiene, or polisoprene) that is shaped to define plunger head 22. As shown in FIG. 1, for some embodiments plunger head 22 may be formed to define an hour glass like shape.

Figure 3:
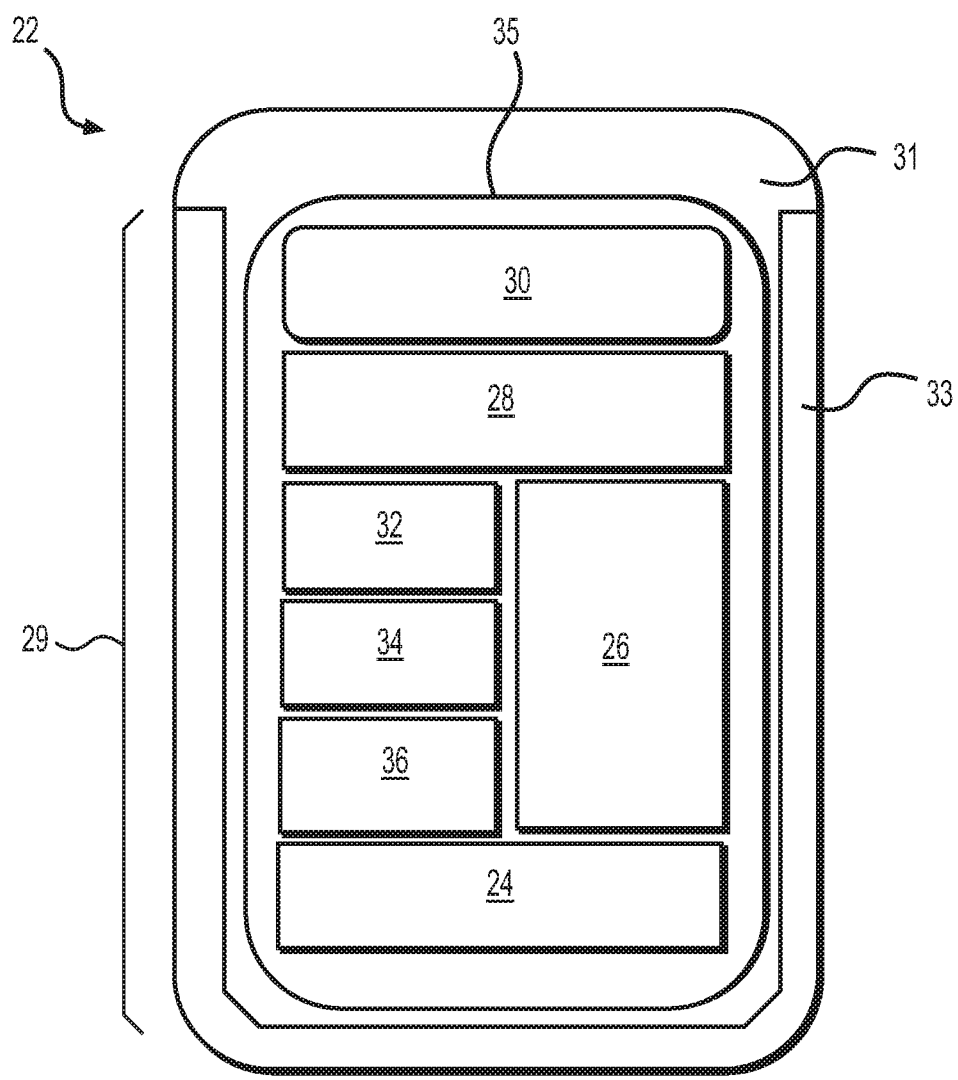
FIG. 3 is a schematic illustrating another embodiment of the plunger head of FIG. 1

In some embodiments, plunger head 22 may formed of a plurality of components. For example, plunger head 22 may be formed of a first component 31 and a second component 33 that may be fixedly (e.g., glued or bonded) or releasably coupled together such that first component 31 and second component 33 may form plunger head 22, as shown in FIG. 3. First component 31 and second component 33 may each take a variety of forms and shapes. FIG. 3 shows a cross-section of one illustrative example where first component 31 may be shaped to define a plug like shape while second component 33 may be shaped to define a bucket like shape configured to receive the plug shaped first component 31. When installed in barrel 12, plunger head 22 may be oriented in barrel 12 such that second component 33 sits below first component 31 such that second component 33 may separate first component 31 from medication 20 contained within barrel 12. As a result, contact with medication 20 within barrel 12 may be limited to second component 33 (i.e., first component 31 may be prevented from contacting medication 20). Such an arrangement may be advantageous because first component 31 and second component 33 may be manufactured from different materials if desired and the available options of materials for first component 31 may be greater because compatibility with medication 20 may be eliminated as a consideration. Second component 33 may be manufactured from elastomers or other materials commonly used to manufacture plunger heads thus reducing or eliminating compatibility concerns, which may reduce and simplify regulatory hurdles and testing. First component 31 may be manufactured from the same material as second component 33 or from different materials including those which may not be compatible with medication 20. For example, second component may be formed of an elastomer (e.g., butyl rubber) while first component may be formed of another plastic, elastomer, or rubber (e.g., silicone rubber).

In some embodiments, as shown in FIG. 3, the electronic components 29, which may include, for example, any combination of, transducer 24, microcontroller 26, power source 28, transceiver 30, and temperature sensor 36, as well as the other electronic components, described herein, may be housed in first component 31. Second component 33 may be a simple elastomer mold or liner designed to separate first component 31 from medication 20. In other words, the electronic components may be isolated from medication 20 within first component 31.

There are a variety of designs and arrangements for plunger head 22 having multiple components (e.g., first component 31 and second component 33), as described herein. In some embodiments, one or more of electronic components 29 may be housed in first component 31 while one or more of electronic components 29 may be housed in second component 33. In some embodiments, plunger head 22 may be constructed of additional components in addition to first component 31 and second component 33. For example, FIG. 4A-4F illustrates several different plunger head 22 designs.

Figure 4A:
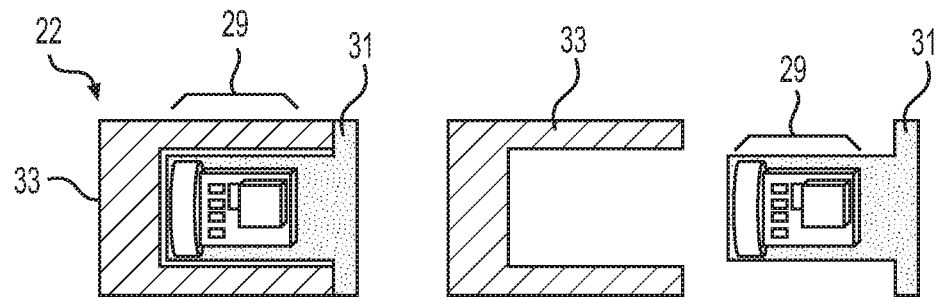
FIGS. 4A-4F are schematic illustrations of different embodiments of plunger heads, according to exemplary embodiments.

FIG. 4A illustrates an embodiment of plunger head 22, similar to FIG. 3, where electronic components 29 may be housed in first component 31 and first component 31 may be inserted into or partially encapsulated by second component 33. As shown in FIG. 4A, first component 31 with electronic components 29 may be "T" shaped and second component 33 may be U-shaped or bucket-shaped such that it may receive first component 31. Bucket-shaped as used herein may refer to any shape that defines a cavity.

Figure 4B:
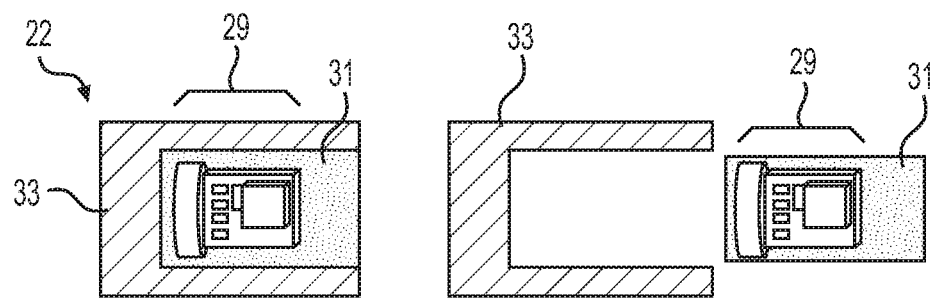

FIG. 4B illustrates another embodiment of plunger head 22, similar to the embodiment of FIG. 4A, except the shape and size of first component 31 may be such that it fills the cavity of second component 33 so that first component 31 and second component 33 are substantially flush and form a substantially flat surface for which plunger 14 may contact when pressed.

Figure 4C:
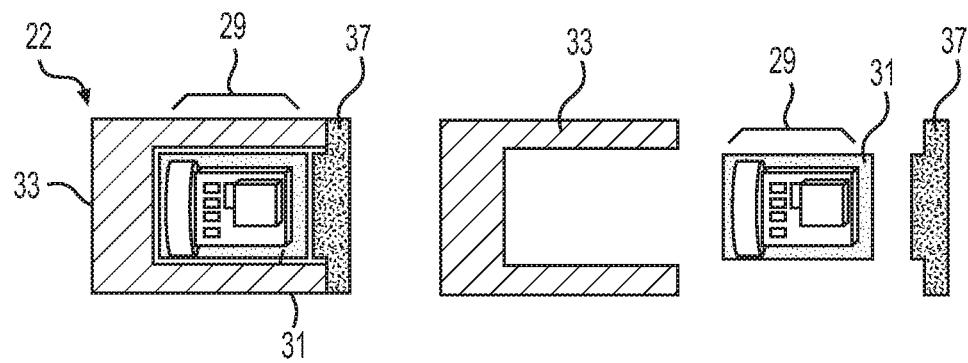

FIG. 4C illustrates another embodiment of plunger head 22, where electronic components 29 may be housed in first component 31 and first component 31 may be inserted into or partially encapsulated by second component 33. According to the embodiment shown in FIG. 4B, first component 31 may fit entirely within the cavity defined by second component 33 and then a third component 37 may cap the cavity and seal first component 31 within second component 33. In some embodiments, third component 37 may be formed of the same material as first component 31 and/or second component 33.

Figure 4D:
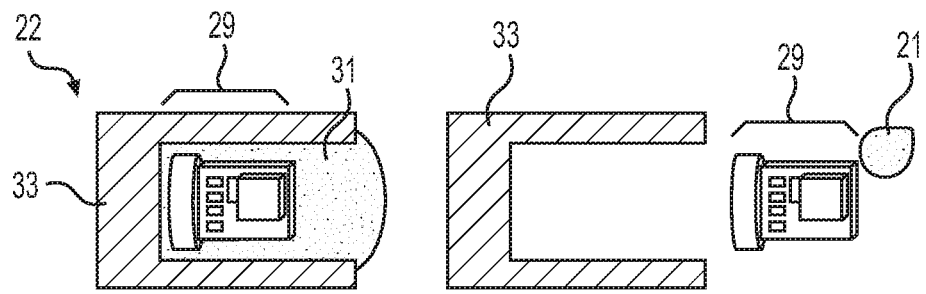

FIG. 4D illustrates another embodiment of plunger head 22. For the embodiment shown in FIG. 4D, electronic components 29 may be inserted into the cavity of second component 33 and polymer 21 may be backfilled into the cavity to surround electronic components 29 and form first component 31.

Figure 4E:
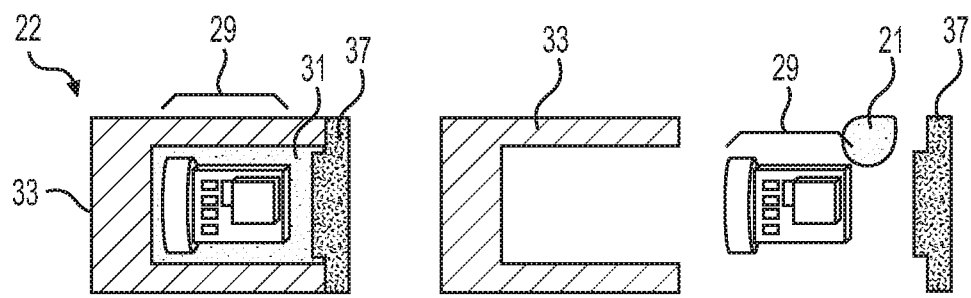

FIG. 4E illustrates another embodiment of plunger head 22, similar to the embodiment of FIG. 4D, except the embodiment in FIG. 4E may be sealed with third component 37.

Figure 4F:
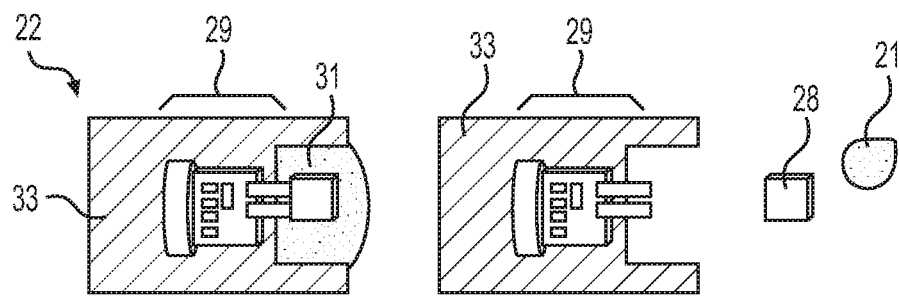

FIG. 4F illustrates another embodiment of plunger head 22. For the embodiment shown in FIG. 4F, a portion of electronic components 29 may be housed in second component 33 and at least one or more of electronic components 29 may be housed in first component 31. For example, transducer 24, microcontroller 26, and transceiver 30 may be housed in second component 33 while power source 28 (e.g., battery or batteries) may be housed in first component 31 and contacts for power source 28 may protrude from second component 33.

Figure 5:
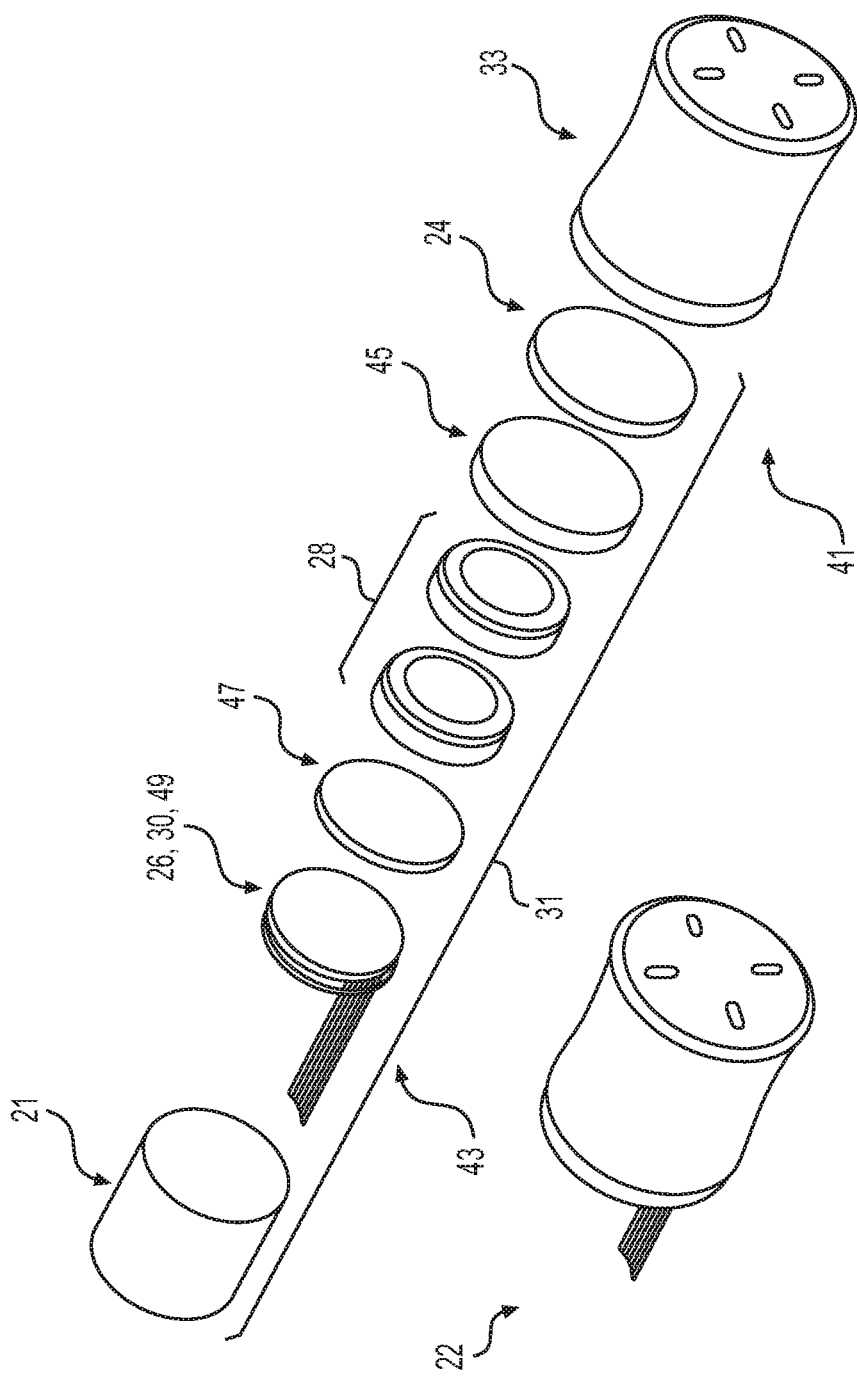
FIG. 5 is an exploded assembly view of a plunger head, according to an exemplary embodiment.

FIG. 5 illustrates an exploded assembly view and assembled view of plunger head 22, according to an exemplary embodiment. As shown in FIG. 5, transducer 24, power source 28, microcontroller 26, and transceiver 30 may be generally cylindrical shaped and arranged in a pancake like stack configuration. As shown in FIG. 5, transducer 24 may be positioned at a distal end 41 of plunger head 22 and microcontroller 26 and transceiver 30 may be positioned at a proximal end 43 of plunger head 22. Plunger head 22 may include one or more elements positioned between transducer 24 and microcontroller 26/transceiver 30, for example, power source 28. As shown in FIG. 5, power source 28 may include one or more batteries. In some embodiments, as shown in FIG. 5, a backing disc 45 may be positioned between power source 28 and transducer 24. Backing disc 45 may be formed of a suitable elastomer or other material, for example, ethylene propylene diene monomer (EPDM), butyl rubber, and nitrile. Backing disc 45 may help acoustically isolation power source 28, microcontroller 26, and transceiver 30 from transducer 24. This may be advantageous because when transducer 24 sends ultrasonic pulses out (i.e., away from distal end 41), energy pulses may also go up toward distal end 41 and then reflect off the different elements, which may produce echoes or interference. Thus, backing disc 45 may help limit the echoes and interference and as result transducer 24 may be able to detect a more uniform response from the ultrasonic pulses.

Plunger head 22 may also include additional elements. For example, as shown in FIG. 5, plunger head 22 may also include a film like disc 47 positioned between power source 28 and microcontroller 26/transceiver 30. Disc 47 may be formed of a variety of suitable materials, including for example, polyimide film.

As shown in FIG. 5, in some embodiments, microcontroller 26 and transceiver 30 may be mounted to a printed circuit board assembly (PCBA) 49. PCBA 49 may be constructed as a rigid circuit board, flex circuit board, or a combination of both (i.e., a rigid-flex circuit board). For example, the core of PCBA 49 may include a rigid circuit board portion and then flexible circuit board portions may extend out from the rigid circuit board portion. The flexible circuit board sections may be designed to fold or twist and include contacts enabling connection to other elements of plunger head 22 (e.g., power source 28, transducer 24). PCBA 49 may also include a flexible tail as shown in FIG. 5, which may extend toward proximal end 43. In some embodiments, although not shown, suitable circuitry wires may also be used to connect PCBA 49 with power source 28 or transducer 24. Although not shown in FIG. 5, crystal oscillator 32, force sensor 34, temperature sensor 36, and/or an accelerometer may also be mounted on PCBA 49.

As illustrated by FIGS. 4A-4F, there are a variety of ways to assembly and construct plunger head 22. For the embodiment shown in FIG. 5, first component 31 could be pre-assembled and encapsulated and then inserted in second component 33. Alternatively, for the embodiment shown in FIG. 5, transducer 24, backing disc 45, power source 28, disc 47, microcontroller 26, and transceiver 30 may be pre-assembled and inserted in second component 33 and then backfilled with polymer 21. For example, in some embodiments, polymer 21 used to backfill may be polyurethane.

The thickness of second component 33 may vary. For example, in some embodiments, the thickness of second component may be about 0.5 millimeters, about 0.6 millimeters, about 0.7 millimeters, about 0.8 millimeters, about 0.9 millimeters, about 1 millimeter, about 1.1 millimeter, greater than about 1.1 millimeter, or less than about 0.5 millimeters.

In some embodiments, second component 33 may be preinstalled in barrel 12 and supplied with syringe 10 while first component 31 may be supplied separately and configured to get inserted into second component 33 while it sits in barrel 12. This arrangement can facilitate the reuse of first component 31 which may house the electronic components. In some embodiments, first component 31 may be coupled to plunger 14 in order to facilitate easy removal of first component 31 after use.

In some embodiments, as shown in FIG. 3, first component 31 may include, among other things, a structural support system 35. Structural support system 35 may be designed to prevent unintended deformation of first component 31 so that mechanical tolerances may be maintained with desired ranges. In addition, structural support system 35 may be designed to protect (e.g., prevent damage) of electronic components 29 due to compressive forces applied to plunger head 22 by plunger 14 when medication 20 is being injected. An upper surface of structural support system 35 may be designed to function as a "push plate" for plunger 14 and may be designed to uniformly distribute the compressive forces applied by plunger 14.

Structural support system 35 may be, for example, a rigid skeleton, cylinder, container, or frame work that surrounds, encloses, or is embedded in one or more of electronic components 29. Although FIG. 3 shows structural support system 35 surrounding all electronic components 29, it is contemplated that in some embodiments, less than all or a portion of electronic components 29 may be contained within or surrounded by a boundary of structural support system 35. As described herein, in some embodiments, first component 31 including structural support system 35 may be encapsulated, over-molded, cast, or sealed within a coating (e.g., elastomer, silicone, plastic, or rubber coating).

In some embodiments, one or more of electronic components 29 may be exposed from first component 31. For example, in some embodiments, a portion of transducer 24 may be exposed from the bottom of first component 31 so that when first component 31 is inserted within second component 33, it mates flush with second component 33.

In some embodiments, first component 31 may also be designed to facilitate proper positioning and orientation of one or more of the electronic components. For example, the shape of first component 31 and second component 33 may be such that when first component 31 is inserted into second component 33, transducer 24 may be pointed generally down a center of barrel 12 when installed. In some embodiments, second component 33 may also be designed to facilitate proper orientation of antenna/transceiver 30 when receiving first component 31.

Structural support system 35 may be made generally semi-rigid or rigid and may be formed of a variety of different materials, for example, plastic, elastomers, composites, metals, or combinations thereof.

In some embodiments, first component 31 may also be arranged to provide additional functionality including, for example, power source 28 (e.g., battery). For example, power source 28 may be positioned such that when no compressive forces are applied to first component 31, then there is no electrical contact between power source 28 and the electronic components, thereby keeping the other electronic components powered down (i.e., conserving power). But when compressive forces are applied to first component 31, power source 28 or one or more of the other electronic components may be moved and brought into electrical contact thereby powering up. In other words, in some embodiments, power source 28 may be positioned within first component 31, such that the compressive force applied by plunger 14 acts as an off/off switch, which initiates (e.g., wakes up or powers up) the electronic components of plunger head 22.

Separating plunger head 22 into first component 31 (that house the electronic components and second component 33 (that contacts the medication) may provide additional advantages. For example, a challenge with monolithic encapsulating or overmolding of electronic components is that the process usually exposes the electronic components to higher temperatures during both the molding step and later sterilization step(s), which may damage the electronic components, in particular, power source 28 (e.g., the battery). By splitting plunger head 22 into separate components (i.e., first component 31 and second component 33), a lower-temperature (e.g., about 60 degrees Celsius or less) series of steps for manufacturing and sterilization can be employed for first component 31, which houses the electronic components, while a higher-temperature (e.g., greater than about 60 degrees Celsius) series of steps for manufacturing and sterilization can be employed for second component 33, which contacts medication 20. The first component 31 and second component 33 may then be attached (e.g., by adhesive, bonding, or friction), or another attachment means to form a completed sealed and sterile plunger head 22.

Although the multiple component arrangements (e.g., first component 31 and second component 33) is described herein with reference to plunger head 22, it is contemplated that this multiple or separate component arrangement may be utilized in other applications where electronic components are being packaged (e.g., encapsulated or over molded) for applications of use where they are alongside sensitive materials (e.g., liquids, medications, chemicals, etc.).

Figure 6:
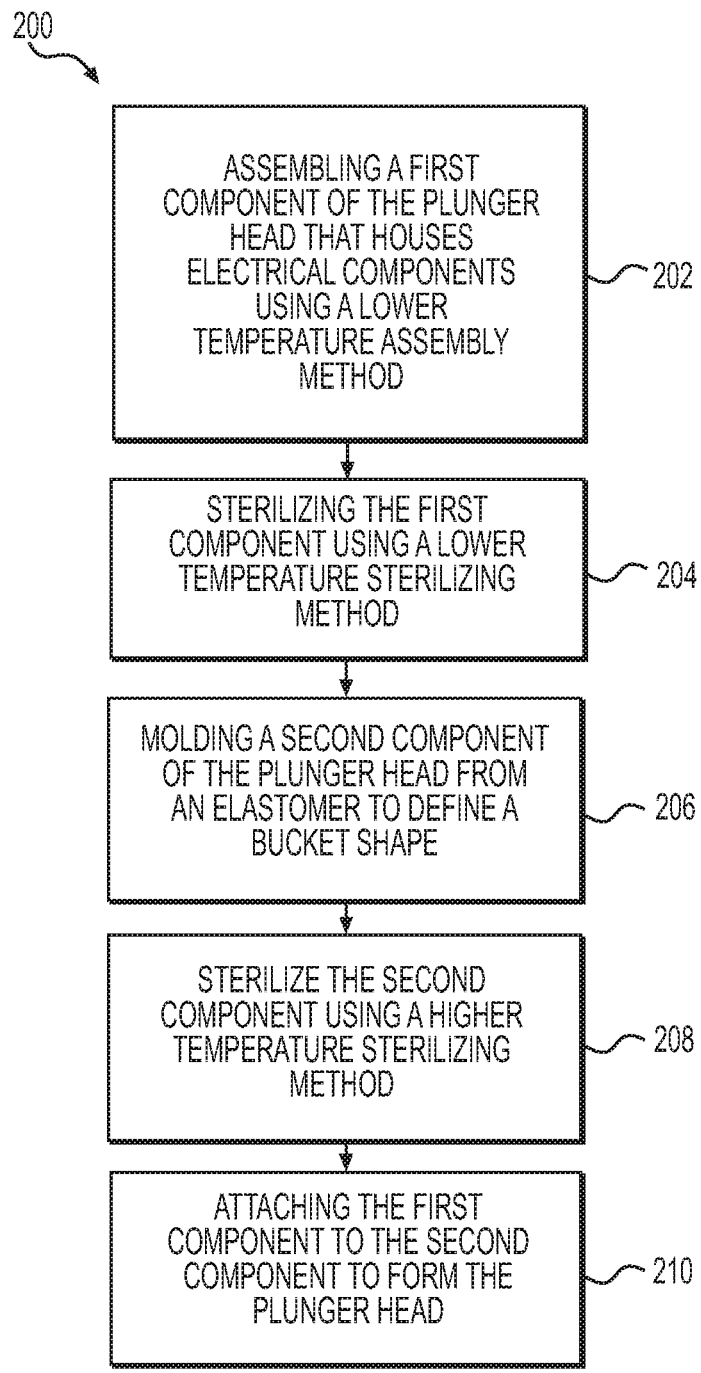
FIG. 6 is a flow chart illustrating a method of manufacturing a plunger head, according to an exemplary embodiment.

A method 200 of manufacturing plunger head 22 formed of first component 31 and second component 33 will now be explained with reference to FIG. 6. Method 200 may include, at step 202, assembling first component 31 of plunger head 22, which houses the electronic components, using a lower-temperature and pressure assembly method and material compatible with the temperature and pressure specifications for electronic components 29. Method 200 may also include, at step 204, sterilizing first component 31 using a lower-temperature sterilization method. Method 200 may also include, at step 206, molding second component 33 of plunger head 22 from an elastomer to define, for example, a bucket shape). Method 200 may also include, at step 208, sterilizing a second component 33 using a higher-temperature sterilization method. Method 200 may also include, at step 210, attaching first component 31 to second component 33 to form plunger head 22. First component 31 and second component 33 may then be attached (e.g., by adhesive, bonding, or friction), or another attachment means to form a completed seal and sterile plunger head 22.

Figure 7:
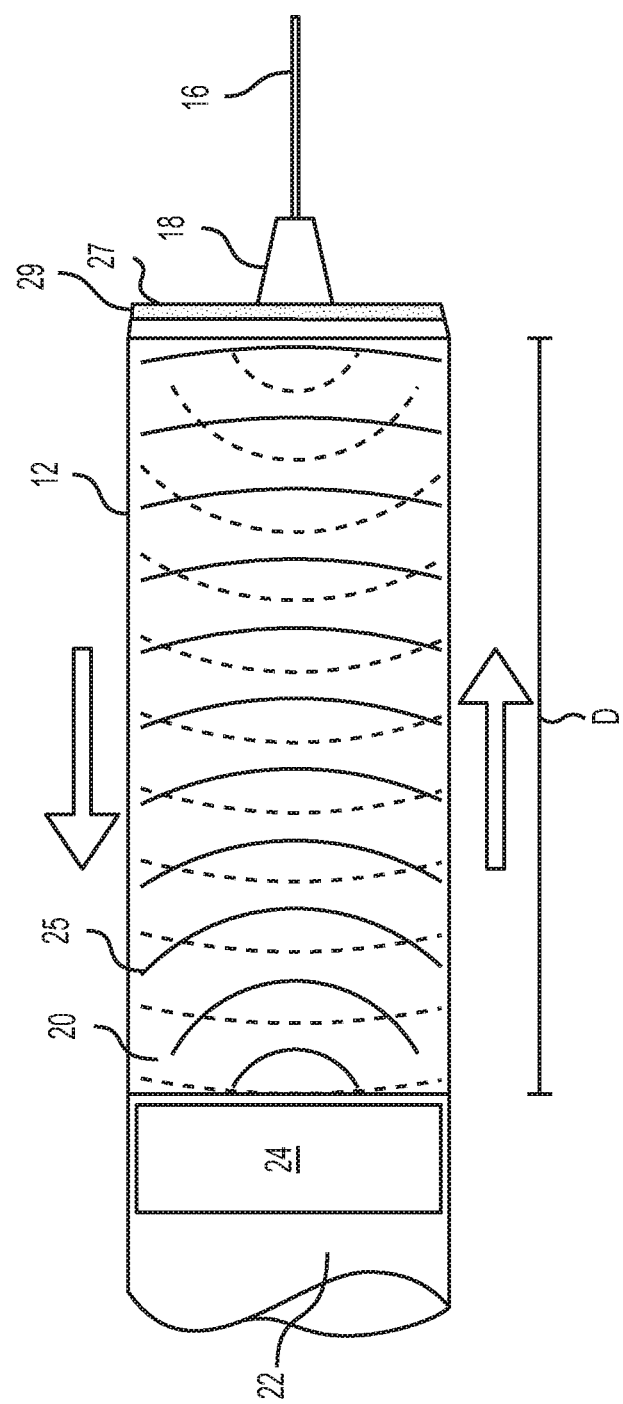
FIG. 7 is a schematic illustrating the behavior of ultrasonic signals transmitted by the plunger head, according to exemplary embodiments.

Transducer 24 may be an actuator, piezoelectric element, or speaker-like voice coil configured to generate and send a pressure wave or ultrasonic signal. Transducer 24 may be sized to be slightly smaller than the inner diameter of barrel 12. As shown in FIG. 7, transducer 24 may be configured to generate ultrasonic signals 25 (e.g., radiated sound energy waves) and send the ultrasonic signals 25 down barrel 12 toward hub 18 and needle 16. The ultrasonic signals can travel through medication 20 along the length of barrel 12 and bounce or reflect off an end 27 of barrel 12 and travel back through medication 20 to plunger head 22. The reflected ultrasonic signals can be received and detected by transducer 24. The speed of sound in medication 20 may be a known value and thus a distance D can be calculated very accurately based on the time it takes for a ultrasonic signal to travel down and back from transducer 24. As plunger head 22 is moved down barrel 12 distance D will change and by knowing the diameter of barrel 12 then the volume of medication 20 dispensed may be calculated based on the change in distance D.

As shown in FIG. 7, in some embodiments, a porous membrane 19 may be placed within barrel 12 at end 27. Porous membrane 19 may be designed to allow medication 20 to pass through while providing a surface with good reflective properties for the ultrasonic signals 25 to reflect from. Utilizing porous membrane 19 may improve the accuracy of the reflective wave detection and thereby the distance and volume calculations. It is contemplated that other materials may be used besides a porous membrane. It is also contemplated that the geometry of barrel 12 at end 27 may dictate whether a porous membrane is needed. For example, in some embodiments the geometry of end 27 may be designed to produce the desired reflective properties avoiding the need to porous membrane 19.

In some embodiments, microcontroller 26 may be configured to use the temperature of medication 20 to compensate for variations in the temperature that would affect the speed of sound within the medication, thus improving the accuracy of the distance and volume calculations.

As described herein, in some embodiments, microcontroller 26 may be mounted to a printed circuit board and may include one or more processors, including for example, a central processing unit (CPU). The processors may include any suitable type of commercially available processor or may be a custom design. Microcontroller 26 may include additional components, for example, non-volatile memory (e.g., a flash memory), volatile memory (e.g., a random access memory (RAM)), and other like components, configured to store information).

Microcontroller 26 may be programmed with instructions to control the operation of transducer 24. Microcontroller 26 may be programmed with instructions to calculate data representative of the quantity of medication 20 dispensed. For example, in some embodiments, microcontroller 26 may be programmed to detect and record the reflection times of the ultrasonic signals 25. Based on the reflection times, microcontroller 26 may track and produce a time profile of the position of transducer 24 (i.e., plunger head 22). Based on the time profile of the position, microcontroller 26 may be able to identify a first distance $D_1$ or starting position (e.g., before medication 20 is dispensed), which may correspond with barrel 12 being filed and a second distance $D_2$ or ending position (e.g., after medication 20 is dispensed), which may correspond with barrel 12 being empty. Microcontroller 26 may then calculate the change in distance between $D_1$ and $D_2$ and based off of the change in distance may calculate the volume (i.e., amount or quantity) of medication 20 dispensed.

In some embodiments, microcontroller 26 may be programmed to automatically differentiate a portion of the volume dispensed as part of an air shot versus the portion of volume injected into a patient. An air shot may be defined as priming of the medication injection device by dispensing a small quantity (e.g., 2 units) of medication 20 into the air prior to injection. An air shot is a common practice associated with medication injection devices and the primary purposes are to remove bubbles from the medication, fill the needle, and clear any potential debris from the needle (e.g., when a needle is reused). Failure to differentiate the volume disposed as part of an air shot could lead to more medication than was actually injected being recorded and this can lead to inaccurate medication injection records. By recognizing and air shot, microcontroller 26 can subtract the volume of medication dispensed during the air shot from the total volume of medication 20 dispensed to determine the actual volume of medication 20 injected in a patient. In some embodiments, the volume of the air shot and the volume of the actual injection may be logged and recorded so a caregiver may monitor if recommended procedures (e.g., an air shot) are being followed.

Microcontroller 26 may be programmed to recognize an air shot using an algorithm based on one or more conditional states. The algorithm may be programmed to recognize a dispensed volume of medication as an air shot when there is a short gap (e.g., about 5 seconds, about 4 seconds, about 3 seconds, about 2 seconds) between a first volume and a second volume of medication being dispensed. In other words, a first volume of medication dispensed when there is a sequence of at least two or more dispensing events in a row may be recognized as an air shot. In some embodiments, the algorithm may also be programmed to incorporate and recognize an air shot base on the volume of the amount disposed. For example, the algorithm may be programmed to recognize a dispensed volume that is about equal to a recommend air shot volume (e.g., 2 units) as an air shot. In some embodiments, the algorithm may also be programmed to incorporate and recognize an air shot based on an orientation of the medical injection device or plunger head 22. For example, in some embodiments plunger head 22 may include an accelerometer that microcontroller 26 may utilize to determine orientation. In some embodiments, the algorithm may also be programmed to incorporate and recognize an air shot based on a rate of pressure decline of medication 20 within barrel 12 after an initial movement of plunger head 22. For example, transducer 24 may function as a piezoelectric element and measure pressure of medication 20. Further it may be determined that a faster pressure decline may correspond with an air shot because for an air shot medication 20 is just being shot in the air against no back pressure. In comparison, when medication 20 is being injected into a patient there is a back pressure caused by the tissue.

In some embodiments, medication 20 may include an active medication ingredient and a buffer solution. The concentration of the active medication ingredient may be known or programmed into microcontroller 26 enabling the specific volume of the active medication ingredient to be calculated. In some embodiments, for example, the concentration of the active medication ingredient may be stored in the non-volatile memory of microcontroller 26. In some embodiments, additional information regarding the medication 20 may also be stored, for example, ultrasonic velocity vs. temperature data.

Transducer 24 and/or microcontroller 26 may be programmed to perform various forms of signal conditioning in order to detect the time of the reflected ultrasonic signals 25. The signal conditioning may include, for example, amplification, filters, and envelope detection. Transducer 24 and microcontroller 26 may use the signal conditioning to determine for example, time to first rising edge or time to maximum reflective value in order to determine the reflection time.

Figure 8:
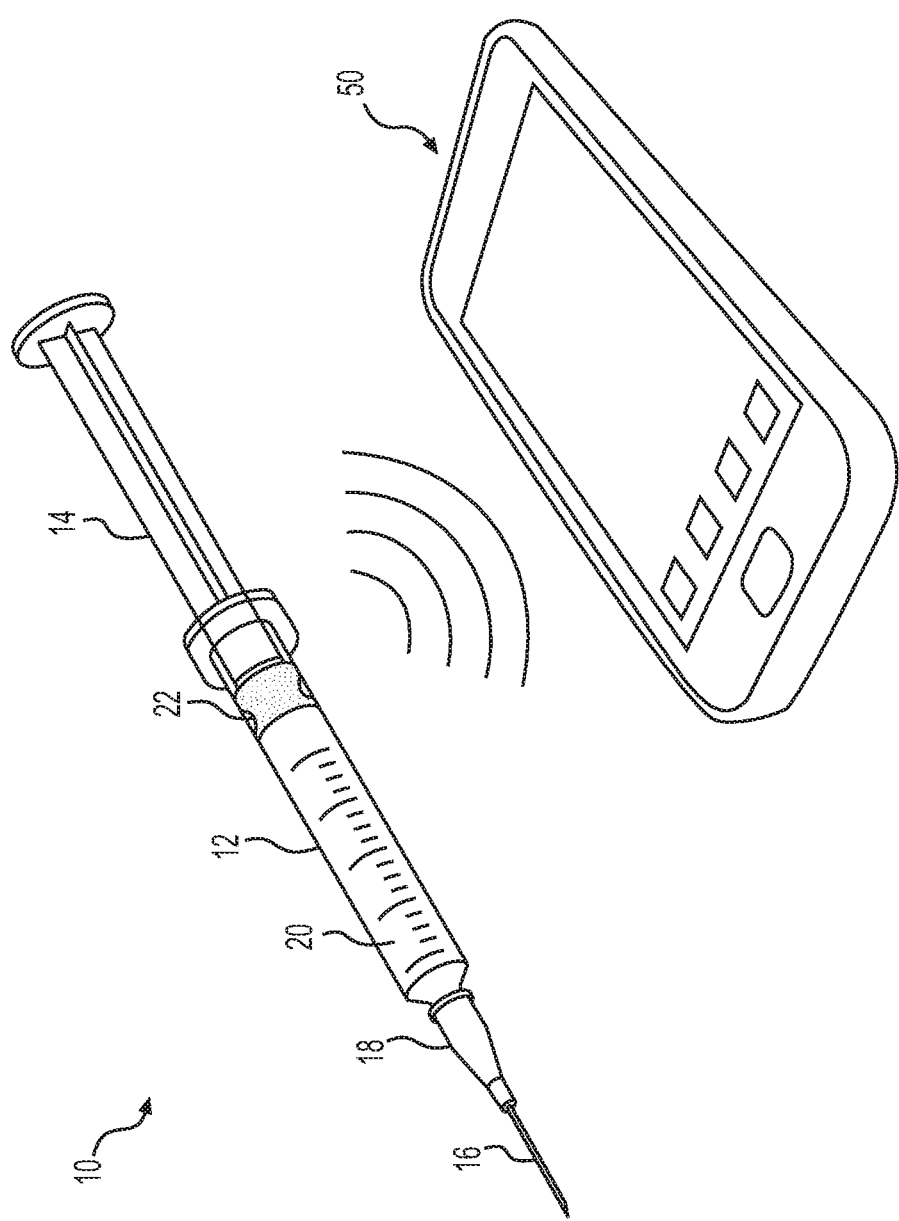
FIG. 8 is a perspective view of the medication injection device of FIG. 1 communicating with a remote device, according to an exemplary embodiment.

Plunger head 22 may transmit data (e.g., the amount of medication 20 dispensed and time and date it was dispensed) to a remote device (e.g., a smart phone, a glucose monitor, an insulin pump, or a computer) via one or more of the wireless communication methods. For example, as shown in FIG. 8, plunger head 22 may transmit data to a remote device 50, which may be a smart phone. Plunger head 22 may have a unique identifier so remote device 50 may be able to identify and process the information received properly. Plunger head 22 may transmit this information to remote device 50 immediately or shortly after the medication is administered or plunger head 22 may store the information until the remote device is paired and within range. The information may be stored, for example, in memory of microcontroller 26. In some embodiments, plunger head 22 may wait to initiate transmitting of the information to remote device 50 until initiated by remote device 50. For example, a user may initiate information retrieval on remote device 50. In some embodiments, remote device 50 may transmit the information to a caregiver (e.g., a doctor) or upload the information to the cloud so it may be saved to the patient's medical history and may be accessed by the caregiver. The ability of a caregiver or a patient to access and review the dose history may improve treatment. For example, the ability of a caregiver to review a diabetic insulin injection history and continuous glucose measurement data may enable the caregiver to adjust the prescribed treatment to improve the therapeutic effect, for example, by better stabilizing the patient's glucose levels.

In some embodiments, plunger head 22 may also include a crystal oscillator 32 configured to keep a real time clock (RTC) so that the date and time of each injection may be accurately recorded and stored in memory of microcontroller 26. Crystal oscillator may be, for example, a 32 kHz crystal oscillator. In some embodiments, microcontroller 26 may include an internal oscillator (e.g., RC oscillator), which may be calibrated using crystal oscillator 32. The internal RC oscillator may be, for example, a 10 MHz RC oscillator. Internal RC oscillator may provide sufficient time accuracy to measure the position (e.g., distance D) of plunger head 22 to within, for example, about 150 microns. In some embodiments, transducer 24 may be used as an oscillator or as a calibrator for the internal RC oscillator. In some embodiments, the frequency of the RC oscillator may be up-converted on microcontroller 26 to a higher frequency. For example, the RC oscillator may be used to drive a higher-frequency phase-locked loop.

In some embodiments, plunger head 22 may be designed to back-interpolate the time of each injection enabling crystal oscillator 32 to be eliminated. In order to maintain the RTC, crystal oscillator 32 may consume a significant amount of power, thus eliminating the crystal oscillator 32 can save a significant amount of power as well as save space.

Plunger head 22 may back-interpolate the time of each injection by relying on the real time clock of the remote device. The method of back-interpolating may start with plunger head 22 taking and logging a series of data samples (e.g., plunger head 22 positions). Plunger head 22 may be programmed to take and log the data samples at an approximately regular interval. The data samples, may be stored, for example in a memory of microcontroller 26 in the order measured. The data samples may be logged and stored into memory with other data values (e.g., calculated injection volume, temperature, etc.). The collection of logged data samples may be transferred/transmitted (e.g., uploaded) to a remote device, which will receive the data samples in the same order. The remote device may rely on the approximately regular interval of the data sample logging to back-interpolate from the actual time at time of transfer, as determined by the RTC of the remote device. By back-interpolating the approximate time of each data sample logged may be determined. For example, if there were six samples transferred to the remote device and they were known to have been captured at about 60 minute intervals then the remote device may determine the time of each of the six samples were logged working backwards from the time of data transfer. However, this example produces about a 60-minute uncertainty in the calculated time of the data sample points because the time of transfer may not be synchronized with the time of data sample logging. However, plunger head 22 may be programmed to log data samples at a faster frequency to reduce the uncertainty or increase the accuracy. For example, data samples may be logged every 30 minutes, 15 minutes, 10 minutes, 5 minutes, 1 minute, or less than 1 minute.

The approximately regular interval may be determined or maintained by a less accurate, less power consuming, smaller timing device (e.g., an oscillator). It is noted that the reduce accuracy of the timing device may result in the approximately regular interval drifting due to a variety of factors, for example, temperature, voltage, or factory determined offsets. However, in some embodiments, plunger head 22 may store the factory determined offsets and be programmed with instructions to measure and log the temperature and/or voltage. Microcontroller 26 may be programmed with instructions to use the factory determined offsets and the logged temperatures and voltages to generate a model to correct drift (i.e., change in interval) between the approximately regular intervals caused by variability in the temperature and the voltage. This same method may also be used in other embodiments to correct drift even in a more accurate time tracking system (e.g., a quartz referenced system).

Although the above described back-interpolation and drift correction method is described in reference to plunger head 22, it is contemplated that this method could be used in other sensor or sampling systems to provide timestamps of useful accuracy for a sequence of sensor samples that do not contain an accurate time reference. This method provides cost, power, and space savings while providing an accurate time reference for a sensor system.

Antenna or transceiver 30 may be used to communicate with a variety of remote devices (e.g., smart phones, glucose monitors, insulin pumps, computers, etc.). Plunger head 22 may transmit the information via any suitable wireless communication method. For example, in some embodiments, plunger head 22 may utilize radio data transmission, BLUETOOTH or BLE, near field communication (NFC), infrared data transmission or other suitable method. In some embodiments, information may also be wirelessly transmitted from a remote device to plunger head 22 via antenna 30. For example, the date and time may be set by writing to microcontroller 26 via the wireless communication.

In some embodiments, plunger head 22 may also include a force sensor 34. Force sensor 34 may be configured to detect when a force is applied to plunger head 22 via plunger 14. Force sensor 34 may be, for example, a simple spring-loaded switch that is molded into the plunger head 22. In some embodiments, transducer 24 may be configured to function as a force sensor thereby eliminating the need for a separate force sensor 34. For example, transducer 24 may have a piezoelectric element that may detect the dynamic changes in pressure when a user depresses plunger 14.

Power source 28 may be any suitable power source. For example, power source 28 may be a battery, a capacitor, or the like. In some embodiments, power source 28 may be rechargeable via wireless energy transmission, for example, inductive coupling, resonant inductive coupling, radio frequency (RF) link, or the like. In some embodiments, power source 28 may be a non-rechargeable battery that is configured to last the storage and operational life of plunger head 22, for which the combined storage and operational life may be about 1 year, about 2 years, about 3 years, or more. For example, in some embodiments, power source 28 may be a watch battery. In some embodiments, where plunger head 22 is a passive device as described herein, power source 28 may be eliminated.

It is common for goods, including medical injection devices, to have a long storage life between the time of manufacture and time of use/sale. Products that include embedded electronics, in particular a battery, it can be a challenge to conserve battery power while the products are in storage. Some products have no on/off switch, buttons, or removable/rechargeable batteries, so the traditional approach of disconnecting or turning off the device while in storage may not be feasible. Also, certain products (e.g., medical injection devices) that include perishable goods (e.g., medication) it may be advantageous to have the product monitor the storage environment (e.g., temperature, light, etc.) and log or store this data and this can't be done if the battery is disconnected.

To address this challenge, plunger head 22 may be designed to enter a low-power sleep mode while in storage. Plunger head 22 may be programmed to enter low-power sleep mode as part of the manufacturing and testing process for plunger head 22 or the medication injection device. When in low-power sleep mode the rate of power consumption may be a fraction of the rate of power consumption for normal operation. While in low-power sleep mode, microcontroller 26 may be programmed with instructions to periodically wake up to measure the temperature. Microcontroller 26 may also log the temperature to create a temperature history. Alternatively, in some embodiments microcontroller 26 may be programmed to log the temperature only when there is a change in temperature, thus saving on data storage. The efficacy of some medications is affected by temperature. For example, insulin is sensitive to hot and cold temperatures. Plunger head 22 thus may monitor the temperature medication 20 through storage and up through use to ensure it stays within an acceptable range. If the temperature of the medication 20 goes outside the acceptable range then plunger head 22 may be configured to send an alert. The type of alert may vary. In some embodiments, plunger head 22 may include a display (not shown in FIG. 2) and the alert may be a flashing light or a visual indicator. In some embodiments, plunger head 22 may include a speaker and the alert may be auditory, for example, a beeping sound. In some embodiments, the alert may be transmitted to a remote device and the remote device may display a visual alert and/or play an auditory alert.

In some embodiments, plunger head 22 may also be designed to utilize the temperature measurement to transition between modes. For example, a medication injection device that includes plunger head 22 and medication 20 may often be stored at a lower-temperature (e.g., below a normal room temperature of about 20 to about 22 degrees Celsius). Subsequently, prior to use, often the temperature will be the medication device, including plunger head 22 and in particular medication 20 will be raised to room temperature because injection of cold fluids can be painful. Thus, usually there will be a transition from a lower-temperature to a higher-temperature shortly before use thereby triggering a change in the mode of plunger head 22.

As described above, in lower power sleep mode plunger head 22 can periodically measure the temperature, thus microcontroller 26 may be programmed to detect the temperature change that is expect prior to use and when detected microcontroller 26 may be programmed to transition plunger head 22 from low-power sleep mode into an initialization mode. Microcontroller 26 may be programmed to pair with a remote device while in the initialization mode. After a successful pairing, microcontroller 26 may be programmed to transition plunger head 22 to an operational mode and start sending and receiving ultrasonic waves and measuring the position of transducer 24. In some embodiments, microcontroller 26 may be programmed to reenter the low-power sleep mode if it is unable pair with a remote device within a certain period of time (e.g., if no remote device is present). Microcontroller 26 may also be programmed to reenter the low-power sleep mode after a period of inactivity (e.g., no measurable change in transducer 24 position after a programmed period of time). Microcontroller 26 may also be programmed to reenter the low-power sleep mode if a subsequent temperature change (e.g., a decrease in temperature from normal room temperature) is detected. Microcontroller 26 may be programmed to transition directly from the low-power sleep mode back to the operational mode if a successful pairing with a remote device has already occurred.

In some embodiments, plunger head 22 may also be configured to detect air bubbles in medication 20. Air bubbles if injected can be deadly so detection of air bubbles is advantageous. In order to detect air bubbles, transducer 24 of plunger head 22 may be configured to detect small ultrasonic echoes created by the reflection of the ultrasonic waves off the air bubbles in addition to the main echo caused by the end of barrel 12. Plunger head 22 may be configured to transmit an alert if air bubbles are detected. The alert may be communicated in the same ways as the temperature alert described above.

In some embodiments, plunger head 22 may also be configured to differentiate, verify, and/or identify medication 20 contained in syringe 10. For example, when barrel 12 is loaded with medication 20, plunger 14 and plunger head 22 may be pulled all the way back to its stopping point and the distance from plunger head 22 to end 27 of barrel 12 may be known enabling microcontroller 26 to solve for the speed of sound of the fluid, which depends on temperature and density. The temperature may be measured by temperature sensor 36 so the density may be determined and based on the density the amount of solids dissolved in the fluid may also be determined. In addition, the viscosity of the medication 20 may be measured based on the amplitude of the reflected ultrasonic signals 25 because more viscous fluids dissipate more energy. In some embodiments, plunger head 22 may also include electrodes 38 connected to microcontroller 26 configured to measure the conductivity of medication 20. In some embodiments, the electrodes 38 may protrude out from the surface of plunger head 22 into barrel 12 where the electrodes 38 may contact medication 20. With the density, conductivity, and viscosity of medication 20 determined, microcontroller 26 may have a sufficient number of properties to profile medication 20. In some embodiments, the profiling may be configured to differentiate medication 20 in order to determine if it from a prescribed class of medication. In some embodiments, the profiling may be configured to verify that medication 20 is the same as the medication that is prescribed for the patient. In some embodiments, the profiling may be configured to identify the medication 20.

According to an exemplary embodiment, plunger head 22 as described herein may be combined with a syringe that has been modified to include a piezo linear motor. The piezo linear motor may be incorporated into the wall of the barrel of the syringe and a piezo element may be incorporated into plunger head 22. The piezo linear motor may be configured to drive or "walk" the plunger head 22 down the barrel of the syringe by driving the piezo element, thereby forcing the medication from the syringe. This embodiment may enable the piezo linear motor to control medication dispensing while plunger head 22 may simultaneously track the amount of medication being dispensed. In some embodiments, plunger head 22 may control the piezo linear motor or plunger head 22 can communication with a remote device that can control the piezo linear motor such that it dispenses a set amount of medication.

Figure 9:
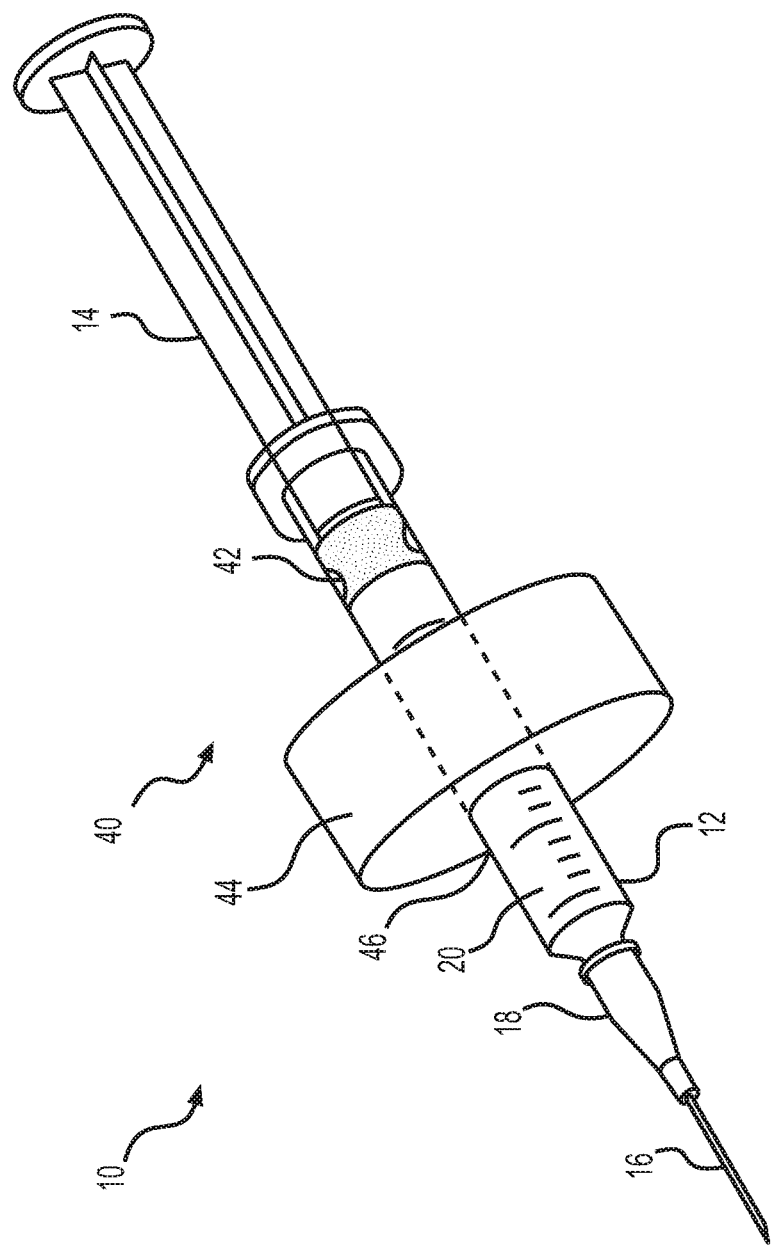
FIG. 9 is a perspective view of a medication injection device, which includes a plunger head and a cuff according to an exemplary embodiment.

FIG. 9 shows a smart syringe system 40, according to an exemplary embodiment. System 40 may be designed for use with a standard disposable syringe 10 or other medication injection devices. Similar to plunger head 22, smart syringe system 40 may be configured to measure and register the quantity of medication 20 administered and the date and time of administration. Smart syringe system 40 may include a smart or intelligent plunger head 42, similar to plunger head 22, and a cuff 44. In some embodiments, plunger head 42 may be designed to be disposable after a single use while cuff 44 is reusable. Embodiments of plunger head 42 designed to be disposable after a single use may houses only the minimum number of components to carry out its function while any optional or ancillary components may be housed in cuff 44 to minimize manufacturing cost of plunger head 42. The manufacturing cost of plunger head 42 may also be minimized by using lower cost components (e.g., transducers, antennas, and microcontrollers) and materials (e.g., rubbers, polymers, plastics) that are less robust and durable, and instead may be designed for shorter operational life spans.

Plunger head 42 may be designed to be supplied with or installed into a disposable syringe 10 and after administering a dose of medication 20, syringe 10 along with plunger head 42 may be disposed of or recycled. In contrast, cuff 44 may be designed to be reused numerous times. For example, a disposable syringe 10 may be inserted through cuff 44 and after medication 20 is administered; cuff 44 may be removed from the used syringe 10 and be saved for later use.

In some embodiments, both plunger head 42 and cuff 44 may be reusable. For example, after medication 20 is administered by syringe 10, both plunger head 42 and cuff 44 may be removed and saved for later use.

Plunger head 42 and cuff 44 can come in different sizes so they may be used with any size syringe. For example, plunger head 42 may be sized to fit within the barrel 12 of any size syringe 10 while cuff 44 may be configured to have a passage 46 configured to receive any size barrel 12 of syringe 10.

Plunger head 42 and cuff 44 (i.e., the smart syringe system 40) in combination may be configured to have some or all of the same components (e.g., a transducer 24, a microcontroller 26, a power source 28, an antenna 30, crystal oscillator 32, force sensor 34, and a temperature sensor 36) as plunger head 22 and perform at least all the same operations as plunger head 22. Some of the components may be housed in plunger head 42 while some of the components may be housed in cuff 44. To reduce the manufacturing cost of plunger head 42, as described above, plunger head 42 may be designed to house the minimum number of components to carry out its functions. For example, system 40 may be configured such that all the components that can be housed in cuff 44 are, rather than plunger head 42. In some embodiments, such components may include a form of memory for data storage.

According to an exemplary embodiment, plunger head 42 may include the transducer 24, antenna 30, and a microcontroller 26 while cuff 44 may also include a separate microcontroller, a power source, and a separate antenna. To reduce complexity, plunger head 42 may be passive (e.g., battery-free) and configured to be controlled and powered by cuff 44 via wireless energy transmission. Cuff 44 may also be configured to communicate with a remote device (e.g., a smart phone, a glucose sensor, an insulin pump, or a computer) thereby enabling the volume of medication and the time and date of administering to be uploaded to another device or the cloud.

In some embodiments, cuff 44 may include a display. Cuff 44 may be configured to display any alerts (e.g., high temperature or improper medication) to the user. Cuff 44 may also display the volume, date, and time after medication has been dispensed. The display may also be configured to allow user input (e.g., touch screen). For example, the user may program in the date, the time, the type of medication or other information.

Figure 10:
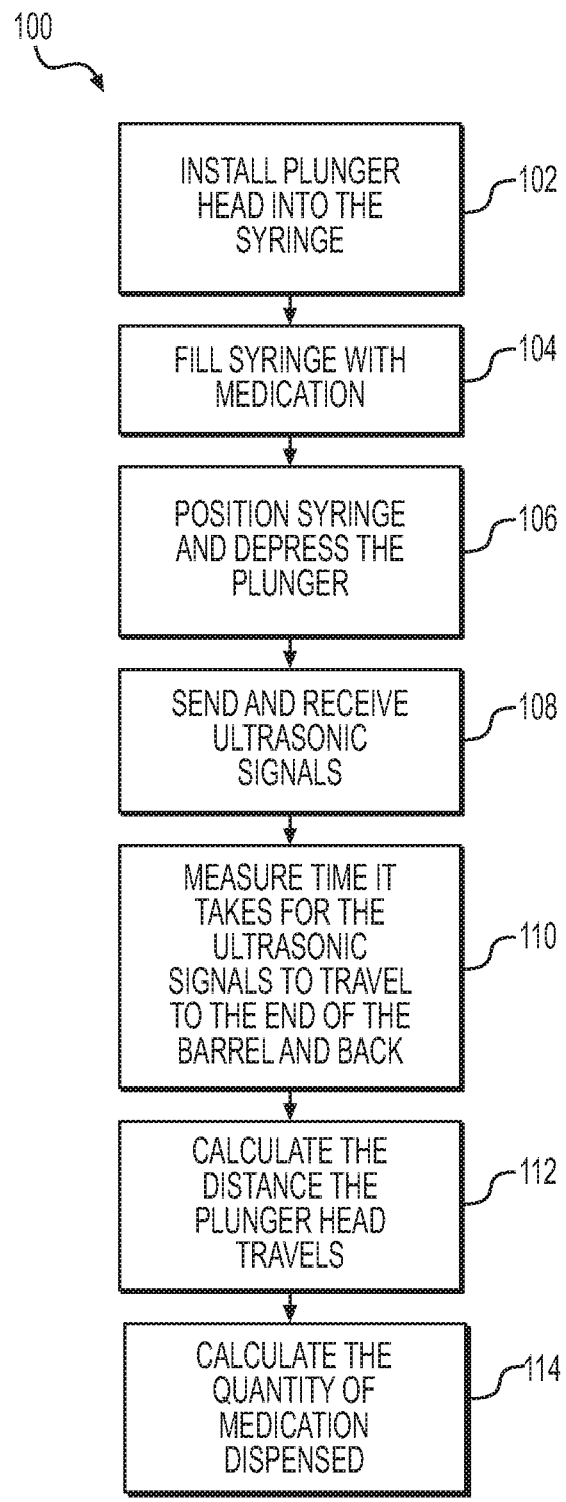
FIG. 10 is a flow chart illustrating a method of tracking administering of medication by a medication injection device, according to an exemplary embodiment.

Plunger head 22 and system 40 described herein may be utilized for a variety of methods for tracking administering of a medication to a patient delivered by syringe. Various methods of utilizing plunger head 22 and system 40 will now be explained with reference to FIG. 10. In some embodiments, the methods as described herein may be performed by a caregiver (e.g., a doctor or nurse) in a hospital or other inpatient setting. In some embodiments, the methods as described herein may be performed by a caregiver (e.g., a doctor, nurse, or parent) at home or outside a hospital. In some embodiments, the methods as described herein may be performed by the patient. It is contemplated that the methods described herein may be performed in other settings by other individuals.

Plunger head 22 may be utilized for a method 100 of tracking administering of a medication to a patient delivered by a medication injection device (e.g., a syringe), according to an exemplary embodiment. In some embodiments, at step 102, method 100 may begin by installing plunger head 22 into barrel 12 of syringe 10 (e.g., a disposable syringe). In some embodiments, syringe 10 may be supplied with plunger head 22 already installed. For embodiments corresponding to other medication injection devices (e.g., insulin pen), plunger head 22 may be installed as part of the original manufacturing process, which may also include loading of medication 20 (e.g., insulin)

Optionally, at step 104, the barrel 12 of the syringe may be filled with the medication 20. This step may be eliminated for embodiments were the medication 20 comes prefilled. The barrel 12 may be completely filled or only partially with medication 20.

At step 106, the syringe may then be positioned for administration. For example, the needle may be inserted into the skin of the patient or into a drug delivery port connected to the patient. Once in position, the plunger 14 of the syringe 10 may be depressed, which forces plunger head 22 down the barrel 12 and forces the medication 20 out the needle 16. Optionally, prior to step 106, method 100 may also include performing an air shot which may be automatically differentiated from the actual injection.

In some embodiments, the initial position of plunger head 22 (e.g., the distance between plunger head 22 and end 27) may be known by plunger head 22. For example, syringe 10 may be full and plunger head 22 may know the distance between plunger head 22 and end 27 when filled. In some embodiments, if syringe 10 is used multiple times to deliver a medication 20, the previous position of plunger head 22 may be known from the last measurement stored. In some embodiments, the initial position of plunger head 22 may be measured using plunger head 22 prior to any medication 20 being delivered, as described below.

Prior to and while plunger 14 is being depressed, plunger head 22 may send and receive ultrasonic signals 25 via transducer 24, at step 108. Plunger head 22 may send and receive ultrasonic signals 25 the duration of the time the plunger is being depressed. Plunger head 22 may measure a time it takes for each of the ultrasonic signals to travel through the medication to an end of the barrel and return to the transducer, at step 110. In some embodiments, at least a portion of the ultrasonic signals 25 may be sent and received before any medication 20 is dispensed enabling the initial position of plunger head 22 and initial volume of medication 20 to be calculated.

As described herein, at step 112, plunger head 22 may calculate the position of plunger head 22 and a distance plunger head 22 travels over the course of dispensing medication 20. At step 114, the quantity of medication 20 dispensed may be calculated based on the calculated distance the plunger head 22 traveled. As described herein, in some embodiments plunger head 22 may automatically differentiate an air shot and if an air shot is performed may subtract the volume of medication 20 dispensed as part of the air shot from the total volume dispensed in order to determine the actual volume of medication 20 injected.

For some embodiments of method 100, the calculation of the quantity of medication dispensed may be performed by a remote device (e.g., a smart phone, a glucose sensor, an insulin pump, or a computer). In some embodiments, method 100 may also include transmitting the quantity of the medication dispensed and the time and date the quantity was dispensed to a remote device. In some embodiments, method 100 may also include uploading the quantity of the medication dispensed and the time and date the quantity was dispensed to the cloud. In some embodiments, method 100 may also include sending the quantity of the medication dispensed and the time and date the quantity was dispensed to a caregiver.

For some embodiments, method 100 may also include logging a plurality of data samples (e.g., position of plunger head 22) at an approximately regular interval and then back-interpolating the time corresponding to each data sample logged to determine the approximate time the quantity of medication 20 was disposed using the RTC maintained by the remote device as a reference time.

Although method 100 is described with reference to plunger head 22, it may also be performed by system 40, as described herein.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described embodiments of plunger head 22, 42 and cuff 44 may be adapted for used with a variety of other medication injection devices, including for example, auto-injectors, auto-syringes, injector pens (e.g., insulin pens), or other drug or medication injection devices.

Although described in relation to an injection device for injecting medication, it is understood that the devices and methods of the present disclosure described herein may be employed with various types of injection devices, including those that may inject or dispense a variety of medication or non-medication fluids in the form of liquid or gas.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Computer programs, program modules, and code based on the written description of this specification, such as those used by the microcontrollers, are readily within the purview of a software developer. The computer programs, program modules, or code can be created using a variety of programming techniques. For example, they can be designed in or by means of Java, C, C++, assembly language, or any such programming languages. One or more of such programs, modules, or code can be integrated into a device system or existing communications software. The programs, modules, or code can also be implemented or replicated as firmware or circuit logic.

Other embodiments will be apparent from consideration of the specification and practice of the embodiments disclosed herein. It is intended that the specification and examples be considered as example only, with a true scope and spirit of the disclosed embodiments being indicated by the following claims.

The invention claimed is:

1. A plunger head for a medication injection device, comprising:
   a first component having a distal end and a proximal end, the distal end being configured for insertion into a barrel of the medication injection device before the proximal end, the first component housing electronic components, wherein the electronic components include:
      a transducer positioned proximate to a bottom side of the distal end of the first component, the transducer being configured to emit ultrasonic signals into the barrel of the medication injection device so that the ultrasonic signals travel along the barrel to an end of the barrel and return to the transducer when the plunger head is placed within the medication injection device; and
      a microcontroller coupled to the transducer and located between the transducer and the proximal end of the first component, the microcontroller being programmed with instructions to calculate data representative of a quantity of a medication dispensed from the barrel of the medication injection device in response to the ultrasonic signals returning to the transducer; and
   a second component at least partially surrounding the first component and separating the first component from the medication contained within the barrel of the medication injection device.

2. The plunger head of claim 1, wherein the second component defines a bucket shape having a cavity at least partially defined by a bottom portion and a radially outer portion of the second component, wherein the first component is positioned within the cavity and the bottom portion of the second component abuts the bottom side of the distal end of the first component.

3. The plunger head of claim 1, further comprising a third component sealing the first component in the second component.

4. The plunger head of claim 1, wherein:
   the first component is formed at least partially of a low temperature polymer; and
   the second component is formed at least partially of a high temperature elastomer,
   wherein the low temperature polymer is a polymer formed and sterilized at or below 60 degrees Celsius, and the high temperature elastomer is an elastomer formed and sterilized above about 60 degrees Celsius.

5. The plunger head of claim 1, wherein:
   the first component is at least partially formed of a silicone rubber; and
   the second component is formed of butyl rubber.

6. The plunger head of claim 1, wherein the first component includes a structural support system protecting the electronic components and configured to control deformation of the plunger head when a compressive force is applied to the plunger head, the structural support system including a skeleton or a frame that at least partially surrounds the electronic components.

7. The plunger head of claim 1, wherein the second component defines a cavity and the electronic components are disposed within the cavity and an elastomer is disposed in the cavity to form the first component.

8. The plunger head of claim 7, further comprising a third component sealing the first component in the cavity of the second component.

9. The plunger head of claim 1, wherein the electronic components include:

a transceiver; and
a power source,
wherein the microcontroller is programmed with instructions to transmit data to a remote device via the transceiver.

10. The plunger head of claim 9, wherein the transducer, the transceiver, the microcontroller, and the power source are all generally disc shaped and arranged in a pancake like stack configuration, and wherein an acoustical isolation disc separates the transducer from the transceiver, the microcontroller, and the power source.

11. The plunger head of claim 9, wherein the transceiver and the microcontroller are mounted to a printed circuit board, thereby forming a printed circuit board assembly, wherein the printed circuit board is a rigid-flex circuit board.

12. The plunger head of claim 1, wherein the transducer is exposed through the bottom side of the distal end of the first component and mates flush with the second component in order to improve ultrasonic signal performance.

13. The plunger head of claim 1,
wherein the data representative of the quantity of the medication dispensed is calculated by:
measuring a first time period for the ultrasonic signals to travel through the medication in the barrel to the distal end of the barrel and return to the transducer;
calculating a distance the plunger head travels based on the first time period;
recognizing an air shot portion of the distance the plunger head travels as corresponding to an air shot; and
calculating the quantity of the medication dispensed based on the distance the plunger head travels and the air shot portion of the distance the plunger head travels.

14. The plunger head of claim 13, wherein recognizing the air shot portion of the distance the plunger head travels is based upon at least one of: a second time period between a first dispensing event and a second dispensing event, the first dispensing event corresponding to an air shot volume, an orientation of the plunger head during the first dispensing event, or a pressure decline rate during the first dispensing event.

15. The plunger head of claim 1, wherein the second component encapsulates a portion of the electronic components, and the first component houses a power source electrically connected to the transducer.

16. The plunger head of claim 15, wherein the power source is electrically connected with at least one contact of the electronic components that protrudes from the second component into the first component.

17. The plunger head of claim 1, wherein the electronic components include a power source that is positioned within the first component such that a compressive force applied to the first component can cause the power source to electrically power the transducer.

18. The plunger head of claim 17, wherein the power source is positioned within the first component such that the compressive force applied to the first component can cause the power source to electrically power the transducer by moving the power source into electrical contact with one or more of the electronic components.

19. A medical injection device, comprising:
a barrel having a reflective surface at a barrel distal end thereof, the reflective surface being configured to reflect ultrasonic signals and to permit a medication to pass through; and
a plunger head, comprising:
a first component having a plunger distal end and a proximal end, the plunger distal end being configured for insertion into the barrel of the medication injection device before the proximal end, the first component housing electronic components, including:
a transducer positioned proximate to a bottom side of the plunger distal end of the first component, the transducer being configured to emit ultrasonic signals into the barrel of the medication injection device so that the ultrasonic signals travel along the barrel, reflect off the reflective surface, and return to the transducer; and
a microcontroller coupled to the transducer and located between the transducer and the proximal end of the first component, the microcontroller being programmed with instructions to calculate data representative of a quantity of medication dispensed from the barrel in response to the ultrasonic signals returning to the transducer; and
a second component at least partially surrounding the first component and abutting the bottom side of the plunger distal end of the first component, the second component being configured to separate the first component from a medication contained within the barrel.

20. A medical injection system, comprising:
a remote device configured for use by a medical caregiver; and
a medication injection device, comprising:
a barrel having a reflective surface at a barrel distal end thereof, the reflective surface being configured to reflect ultrasonic signals and to permit a medication to pass through; and
a plunger head configured for insertion into the barrel, the plunger head comprising:
a first component having a plunger distal end and a proximal end, the plunger distal end being configured for insertion into the barrel of the medication injection device before the proximal end, the first component housing electronic components, comprising:
a transducer positioned proximate to a bottom side of the plunger distal end of the first component, the transducer being configured to emit ultrasonic signals into the barrel of the medication injection device so that the ultrasonic signals travel along the barrel to the barrel distal end, reflect off the reflective surface, and return to the transducer;
a microcontroller coupled to the transducer and to the remote device, the microcontroller being located between the transducer and the proximal end of the first component, the microcontroller being programmed with instructions to calculate data representative of a quantity of the medication dispensed from the barrel in response to the ultrasonic signals returning to the transducer and to transmit the data to the remote device; and
a transceiver coupled to the microcontroller; and
a second component at least partially surrounding the first component and abutting the bottom side of the plunger distal end of the first component, the second component being configured to separate the first component from a medication contained within the barrel, wherein the microcontroller is programmed with instructions to transmit data representative of the quantity of the medication dispensed to the remote device via the transceiver.

* * * * *